United States Patent [19]

McGarrity et al.

[11] Patent Number: 5,162,540

[45] Date of Patent: Nov. 10, 1992

[54] PROCESS FOR THE PRODUCTION OF (+) BIOTIN

[75] Inventors: John McGarrity; Leander Tenud, both of Visp, Switzerland

[73] Assignee: Lonza Ltd., Gampel, Switzerland

[21] Appl. No.: 777,914

[22] Filed: Oct. 17, 1991

Related U.S. Application Data

[60] Continuation of Ser. No. 271,180, Jan. 10, 1989, Pat. No. 5,117,003, which is a division of Ser. No. 134,210, Dec. 16, 1987, Pat. No. 4,876,350.

[30] Foreign Application Priority Data

Dec. 18, 1986 [CH] Switzerland .................. 5051

[51] Int. Cl.$^5$ .......................................... C07D 473/28
[52] U.S. Cl. .................. 548/303.1; 548/110; 548/111
[58] Field of Search .......................................... 548/303

[56] References Cited

U.S. PATENT DOCUMENTS 2,489,235 11/1949 Goldberg ........................ 260/309

FOREIGN PATENT DOCUMENTS 0154225 9/1985 European Pat. Off. .
0161580 11/1985 European Pat. Off. .
0173185 10/1986 European Pat. Off. .
2058234 6/1971 Fed. Rep. of Germany .
2058248 6/1980 Fed. Rep. of Germany .
45-37776 11/1970 Japan .
46-3580 1/1971 Japan .
50-14692 2/1975 Japan .

OTHER PUBLICATIONS

Chemical Abstracts, vol. 74, (1971), 100018h.
Lowe, G., et al., J. Chem. Soc., Perkin Trans. I, (1973), pp. 2907–2910.

*Primary Examiner*—Johann Richter
*Attorney, Agent, or Firm*—Fisher, Christen & Sabol

[57] ABSTRACT

(3aS,6aR)-[(R)-(1-phenylethyl)-3,4-methoxybenzyl dihydro-1H-furo-[3,4-d]-imidazol-2,4(3H,3aH)-dione and 1H-furo-[3,4-d]-imidazol-2,4-(3H,3aH)-dione derivatives which are useful as intermediates for preparing (+) biotin, also known as vitamin H.

2 Claims, No Drawings

PROCESS FOR THE PRODUCTION OF (+) BIOTIN

This is a continuation of application Ser. No. 271,180, filed on Jan. 10, 1989, now U.S. Pat. No. 5,117,003 which is a divisional of prior application Ser. No. 134,210, filed on Dec. 16, 1987, now U.S. Pat. No. 4,876,350.

BACKGROUND OF THE INVENTION

1. Field Of The Invention

The invention relates to a new process for the production of (+) biotin.

2. Background Art (+) Biotin is a human vitamin which is known as vitamin H. But (+) biotin is also used as a pharmaceutical agent for the treatment of dermatosis and as a feed additive with growth-increasing action for domestic animals.

Various processes have been described in the prior art for the production of (+) biotin.

A process is known from U.S. Pat. No. 2,489,232 according to which racemic biotin is produced. But since, as is known, only the optically active (+) biotin is biologically active, the racemic biotin thus produced must then still be separated into the optical enantiomers. On the one hand, in this case all reaction steps are performed with racemic materials, as a result of which the doubled amounts of substance must be processed. On the other hand, resolution of the racemic biotin into the corresponding enantiomers is a very complicated process, which in addition is also unprofitable, since the undesirable enantiomer practically no longer racemizes and can no longer be fed back into the process.

An improvement of such process is known from U.S. Pat. No. 2,489,235. In this case, the resolution of the racemates is already performed in an earlier step, but still this process has the drawback that most of the reaction steps are performed with racemic material and here too the undesirable enantiomer resulting from this resolution practically no longer racemizes and can no longer be fed back to the process.

M. Murakami et al. have developed an improved product for the production of dl-biotin (see Japanese Published Patent Document Nos. 31,669/1970, 37,775/1970, 37,776/1970 and 3,580/1971). The improvement consists in introducing a carboxybutyl group in the 4 position of the dl-1,3-dibenzylhexahydrothieno [3,4-d]-imidazol-2,4-dione. This dione is reacted with a 1,4-dihalomagnesium butane and then carboxylated with carbon dioxide.

Gerecke et al. German Patent No. 2,058,248, have developed a further improvement, by already producing—in an earlier step by optical resolution of a triethylamine salt of the following formula, in which R represents a cholesteryl radical, or of an ephedrine salt of the following formula, in which R represents a cyclohexyl radical:

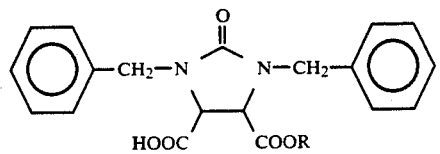

and by further conversion with alkali metal boron hydrides—an optically active lactone of the formula:

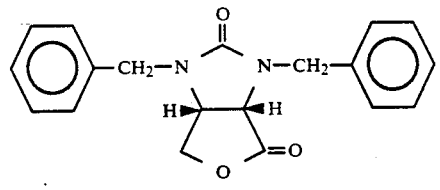

is produced as an optically active intermediate product.

A significant drawback for an industrial use consists in the use of the expensive optically active compounds chloresterol and ephedrine as well as expensive alkali metal boron hydrides. The processes of European Published Application Nos. 0161580 and 0173185 are tainted with the same drawback, namely, the use of expensive optically active compounds.

Moreover, it is known from European Published Application No. 0154225 to produce biotin from 1,3-dibenzylhexahydro-1H-thienoimidazoldiones by a special Grignard reaction with a trioxaadamantylbutylmagnesium bromide, a subsequent dehydration and by cleavage of the corresponding protective groups. This process is just as unfavorable for an industrial process especially because of its expensive Grignard compounds.

BROAD DESCRIPTION OF THE INVENTION

The object of the invention is to provide a process producing (+) biotin starting from an easily-available intermediate product with an industrially-feasible process by means of few reaction steps.

The object of the invention is obtained with the process according to the invention wherein a compound of the formula:

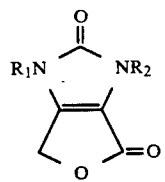

wherein $R_1$ is an (R)- or (S)-1-phenylalkyl group, an (R)- or (S)-1-alkoxycarbonyl-1-phenylmethyl group or an (R)- or (S)-1-aryloxycarbonyl-1-phenylmethyl group, and $R_2$ is hydrogen, a substituted or unsubstituted alkanoyl group, an unsubstituted or an substituted benzoyl group, a substituted or an unsubstituted benzyl group, an alkoxycarbonyl group, an aryloxycarbonyl group, an aryloxyalkyl group, an alkoxyalkyl group, a pyranyl group, an unsubstituted or substituted benzenesulfonyl group, an alkylsulfonyl group, a diarylphosphinyl group, a dialkoxyphosphinyl group or a trialkylsilyl group, is catalytically hydrogenated with hydrogen, the desired diastereomer of the formula:

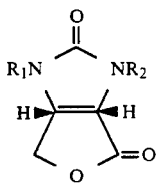

II is separated, if $R_2$ is H, a protective group is introduced by reaction with substituted or unsubstituted aliphatic or aromatic acid chlorides, aliphatic or aromatic carboxylic acid anhydrides, haloformic acid esters, benzyl halides, 1-alkoxyalkyl halides, aromatic or aliphatic sulfonic acid halides, diarylphosphinic acid halides, phosphoric acid dialkyl ester chlorides, substituted or unsubstituted trialkyl silyl halides or substituted or unsubstituted trialkyl silyl acetamides, the desired diastereomer is converted by a further reaction with a thiocarboxylic acid salt derivative into the corresponding thiolactone, the latter thiolactone is reacted either with a Grignard reaction and subsequent splitting off of water or with a compound of the formula:

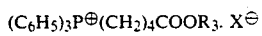

III wherein $R_3$ is H or alkyl with 1 to 4 C atoms and X represents a halogen atom, in the presence of a base to a compound of the formula:

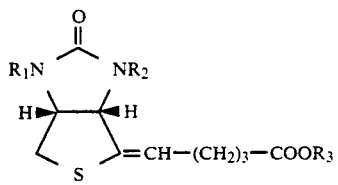

IV wherein $R_3$ has the above-mentioned meaning, in a following step this compound is catalytically hydrogenated with hydrogen and then converted into the end product by cleavage of the protective groups.

When $R_1$ is a 1-phenylalkyl, it is preferably 1-phenyl-($C_2$-$C_4$)-alkyl and most preferably 1-phenylethyl, is a 1-alkoxycarbonyl-1-phenylmethyl, it is preferably 1-($C_1$-$C_4$)-alkoxy-carbonyl-1-phenylmethyl, and is a 1-aryloxycarbonyl-1-phenylmethyl, it is preferably a 1-benzyloxy-carbonyl-1-phenylmethyl- or 1-phenyloxycarbonyl-1-phenylmethyl group.

When $R_2$ is an alkanoyl, it can be ($C_1$-$C_4$)-alkylcarbonyl, preferably acetyl. The alkanoyl group can be substituted by halogen atoms preferably by chlorine. A preferable representative is the trichloroacetyl group. The benzoyl group and the benzyl group is preferably not substituted but substituents like halogenatoms, lower alkyl groups or lower alkoxy groups are not excluded. For example, a p-methoxybenzyl or a methylbenzyl can be applied as substituted benzyl group. When $R_2$ is an alkoxycarbonyl, it can be ($C_1$-$C_4$)-alkoxycarbonyl and aryloxycarbonyl, preferably phenyloxycarbonyl. When $R_2$ is an alkoxyalkyl, it is preferably ($C_1$-$C_4$)-alkoxymethyl. The benzolsulfonyl preferably is p-toluolsulfonyl. The alkylsulfonyl preferably is methylsulfonyl.

Generally the term alkoxy or alkyl defines an ($C_1$-$C_4$)-alkyl group and the term aryl defines benzyl or phenyl, preferably unsubstituted.

A crucial importance for the process is taken on in this case by the new 1H-furo-[3,4-d]-imidazole-2,4(3H,3aH)-diones of the formula:

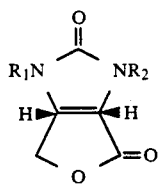

II wherein $R_1$ and $R_2$ have the above-mentioned means, but especially it is taken on by the (3aS, 6aR)-[(R)-(1-phenylethyl)]-3-benzyldihydro-1H-furo-[3, 4-d]-imidazole-2,4(3H, 3aH)-dione of the formula:

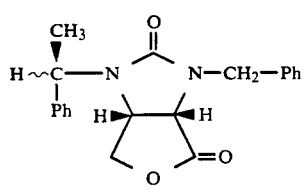

VII and the (3aS, 6aR)-(R)-(1-phenylethyl)]-3-4-methoxybenzyl dihydro-1H-furo-[3,4-d]-imidazol-2,4(3H,3aH)-dione

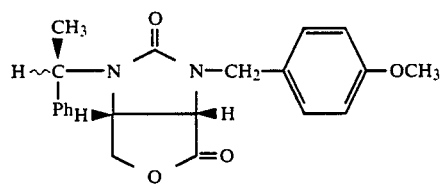

DETAILED DESCRIPTION OF THE INVENTION

The initial products of the formula:

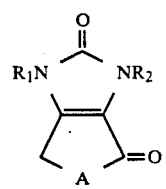

I can be produced according to the commonly-owned U.S. patent application Ser. No. 127,052, filed on Dec. 1, 1987, (LP 1382) Inventors: John McGarrity, Leander Tenud and Thomas Meul, entitled: Imidazole Derivatives And A Process For Their Production, (which is based upon Swiss Patent Application No. 4790/86) the pertinent parts of which are incorporated herein by reference, from tetronic acid according to the following diagram:

DIAGRAM 1

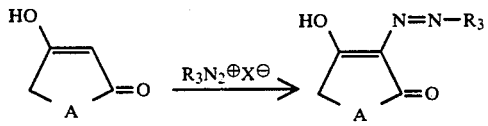

-continued

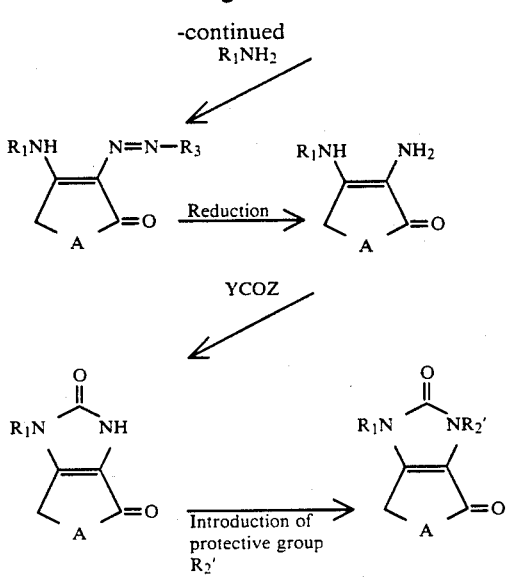

In the diagram 1:
A is S or O
R$_3$ is substituted or unsubstituted phenyl
X is halogen, BF$_4$, or HSO$_4$
Y=Z=chlorine, imidazolyl
Y is chlorine
Z is aryloxy or alkoxy
R$_1$ and R$_2$ have the above-mentioned meaning If R$_2$ is H, according to said commonly-owned U.S. patent application Ser. No. 127,052 (based upon Swiss Patent Application No. 4790/86), a protective group can first be introduced before hydrogenation according to the invention.

The hydrogenation of compound I is catalytically performed with hydrogen, namely, so that the diastereomer of the formula:

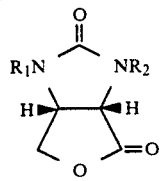    II which has a (3aS, 6aR) configuration, is preferably formed.

Suitable platinum, palladium, rhodium, ruthenium, or nickel catalysts are used, optionally on a support material such as carbon, silicon dioxide, aluminum oxide, aluminum silicate or calcium carbonate. The preferred catalyst of this group is rhodium on aluminum oxide as support.

Just as usable are homogeneous catalyst consisting of rhodium or iridium with ligands such as triphenylphosphine or cyclooctadiene.

The stereoselectivity greatly depends upon the hydrogenation catalysts and upon the respective substituent R$_1$. Thus, for example, the diastereomer II with R$_1$ being (S)-1-phenylethyl can be obtained by use of a palladium catalyst and with R$_1$ being (R)-1-phenylethyl by use of a platinum catalyst.

The catalyst concentration on the support is usually between 1 and 100 percent, preferably between 1 and 10 percent. The catalyst is suitably added to the reaction in an amount of 1 to 50 mol percent, preferably between 1 and 10 mol percent.

The reaction is usually performed in a solvent. There are suitably available for this purpose lower aliphatic alcohols such as ethanol and propanol, lower aliphatic carboxylic acids such as acetic acid, ethers such as diethyl ether, tetrahydrofuran and dioxane, carboxylic acid amides such as dimethylformamide and dimethylacetamide, carboxylic acid esters such as ethyl acetate, or halogenated hydrocarbons such as dichloromethane.

The reaction can be conducted at normal pressure, but the reaction is advantageously performed under pressure. The pressure can vary in a range of suitably 1 to 70 bars, preferably 5 to 30 bars.

Of course, depending on the solvent, the reaction temperature can be between $-25°$ and $+100°$ C.

To obtain the desired optically active diastereomer the reaction solution is suitably freed first from the catalyst, then from the solvent, and the residue then is separated from the undesired diastereomer (3aR—, 6aS isomer) by recrystallization in a suitable solvent.

Acetic acid alkyl esters such as ethyl acetate, or lower alcohols such as ethanol or toluene are appropriately used as suitable solvents.

If compound II is present with R$_2$ being H, the hydrogen is suitably protected with a protective group before conversion into the thiolactone.

The introduction of the protective group R'$_2$ suitably takes place by reaction of compound V with substituted or unsubstituted aliphatic or aromatic acid halides, such as acetyl chloride, propionyl chloride or benzoyl chloride, with benzyl halides or with substituted benzyl chlorides such as p-methoxybenzyl chloride, with cloroformic acid esters, such as chloroformic acid ethyl ester, chloroformic acid benzyl ester chloroformic acid tert-butyl ester or chloroformic acid phenyl ester, with phosphorus compounds such as diphenylphosphinic acid chloride or phosphoric acid diethyl ester chloride, with aromatic or aliphatic sulfonic acid halides such as methanesulfonic acid chloride, p-toluenesulfonic acid chloride or benzenesulfonic acid chloride, with silyl compounds, such as bis(trimethylsily) acetamide, trimethylsilyl chloride, or tert-butyl dimethylsilyl chloride, with alkoxyalkyl halides such as methoxymethyl chloride, or with enol ethers such as dihydropyran. Just as suitable are substituted or unsubstituted aliphatic or aromatic carboxylic acid anhydrides such as acetic anhydride.

The introduction of the protective groups can take place according to known methods, consequently, it is not gone into further.

Compound II protected with the protective group R'$_2$ can be converted into the corresponding thiolactone by reaction with a thiocarboxylic acid salt derivative.

The reaction for R$_1$ and R$_2$ each being benzyl is known from German Patent No. 2,058,234.

Alkaline-earth or alkali salts of aliphatic or aromatic thiocarboxylic acids, such as potassium thioacetate, sodium thioacetate, potassium thiobenzoate or sodium thiobenzoate, can suitably be used as thiocarboxylic acid salt derivatives. Potassium thioacetic is preferably used.

Additionally, crown ethers, such as 18-crown-6, are advantageously used as catalysts.

The reaction is advantageously performed in an inert organic solvent at a temperature between 80° and 200° C.

Depending upon the temperatures, high-boiling solvents such as dimethylformamide or dimethylacetamide as high-boiling amides, substituted anilines such as lutidine, high-boiling amines, or toluene as a high-boiling hydrocarbon are available as solvents. Of course, low-boiling solvents can also be used. Then the reaction is suitably performed under pressure.

The desired thiolactone can be obtained in good yields by the working up usual for a man skilled in the art.

The further reaction of the thiolactone with a Grignard reaction and then splitting off of water was already described for $R_1$ and $R_2$ each being benzyl in German Patent No. 2,058,234.

For the process according to the invention it has proved suitable to use the Grignard reagent a compound of the formula:

XMg—(CH$_2$)$_4$—MgX wherein X is chlorine or bromine.

In a second step the carboxyl group can be introduced into the side chain by treatment with carbon dioxide. Finally, the conversion into compound IV takes place by the splitting off of water, suitably in an acid medium. Use of p-toluenesulfonic acid has proved advantageous.

The further conversion of thiolactone to compound IV can also take place with compound III by means of a Wittig reaction. This was already described in European Published Patent Document No. 0084377 for $R_1$ and $R_2$ each being benzyl.

Thus, the thickness is suitably converted by reaction with compound III of the formula:

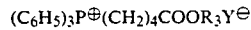

(C$_6$H$_5$)$_3$P$^\oplus$(CH$_2$)$_4$COOR$_3$Y$^\ominus$     III wherein $R_3$ is H or alkyl with 1 to 4 C atoms and X is a halogen atom, in the presence of a base to a compound of the formula:

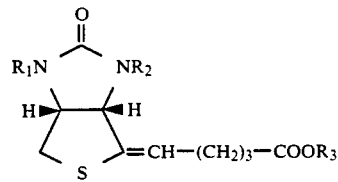

IV

The preferred compound of formula III is carboxybutyl triphenylphosphonium bromide.

Compounds III are used, relative to 1 mol of thiolactone, suitably in amounts of 1 to 5 mol, preferably 1.5 to 2.5 mol.

As suitable bases for formation of the Wittig reagent of compounds III there are used alkylalkali metals such as butyllithium, alkali metal hydrides, such as sodium hydride or potassium hydride, compounds of formula:

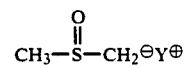

CH$_3$—S—CH$_2$$^\ominus$Y$^\oplus$ wherein Y is an alkali metal atom, such as sodium dimethylsulfinylcarbanion, alkali metal alkoxides such as sodium methoxide or potassium tert-butoxide, alkali metal alkyl amides such as lithium diisopropylamide, alkali metal amides such as sodium amide, alkali metal hydroxides such as sodium hydroxide, carbonates such as sodium carbonate, or silicon compounds such as alkali metal hexamethyldisilazides.

In choosing the solvent, care is to be taken that it does not react with other reaction participants. Suitable for this purpose are ethers such as tetrahydrofuran, dioxane, dimethoxyethane or diethyl ether, aromatic hydrocarbons such as toluene, benzene, chlorinated hydrocarbons such as dichloromethane, or also dimethylsulfoxide.

Suitably, the reaction temperature should be between $-50°$ and $+100°$ C., preferably between $0°$ and $++80°$ C.

After the reaction is finished, it is advantageously acidified and worked up in the usual way. The subsequent reduction of compound IV is suitably performed catalytically with hydrogen according to European Published Document No. 0084377.

Palladium, platinum, ruthenium and rhodium on the usual support materials such as carbon, clay, etc., suitably serve as the catalysts. Raney nickel is just as suitable.

The amount of catalyst suitably varies between 1 and 20 mol percent, relative to 1 mol of IV.

The work is advantageously performed in aromatic hydrocarbons such as toluene, aliphatic alcohols such as methanol, ethanol, n-propanol, isopropanol, carboxylic acid esters such as ethyl acetate, or ethers such as tetrahydrofuran, dioxane, or also in water or acetic acid.

The hydrogen pressure is suitably selected in a range of 5 to 80 bars, preferably 10 to 60 bars. Normal pressure can also be used. The hydrogenation temperature is suitably between $20°$ and $150°$ C., preferably between $40°$ and $80°$ C.

The working up can take place in the usual way by separation of the catalyst and removal of the solvent.

The resultant product of the formula:

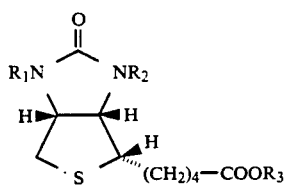

V corresponds to the optically-active precursor of biotin. To free the desired product, the protective groups can be cleaved off by treatment with methanesulfonic acid with heating according to the teaching of Japanese Patent Publication Nos. 31669/1970 and 27279/1978 and U.S. Pat. No. 5,437,973.

If $R_3$ of formula V is an ester function, it will be present unchanged after cleavage of the protective group, so that to obtain biotin a treatment with bases such as sodium hydroxide or potassium hydroxide should suitably follow.

Another method consists in treating compound V with an aqueous mineral acid, preferably HBr, at $30°$ to $90°$ C. Cleavage of the protective groups and the ester hydrolysis can thus be achieved simultaneously.

As a result of the protective group cleavage, after the usual working up, d-(+) biotin of the formula:

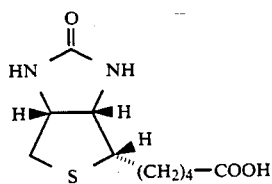

is obtained.

As used herein all percentages, ratios, properties and parts are on a weight basis unless otherwise stated herein or otherwise obvious herefrom to one skilled in the art.

EXAMPLE A (1) Production of (3aS,6aR)-1-[(R)-(1-phenylethyl)]-dihydro-1H-furo-[3,4-d]-imidazol-2,4(3H,3aH)-dione A solution of 8.98 g (36.8 mmol) of 1-[(R)-(1-phenylethyl)]-1H-furo-[3,4-d]-imidazol-2,4(3H,6H)-dione in 90 ml of dimethylformamide was placed in a 250-ml autoclave and 0.90 g of Rh/Al$_2$O$_3$ (5 percent) is added. Then the autoclave was flushed twice successively with hydrogen, and filled to 40 bars. The mixture was stirred for 10 hours. Then the catalyst was filtered off. The solvent was evaporated at 13.3 mbar and the residue was recrystallized with 10 ml of ethyl acetate. (3aS,-6aR)-1-[(R)-(1-phenylethyl)]-dihydro-1H-furo-[3,4-d]-imidazol-2,4(3H,3aH)-dione was obtained as a white crystalline product in a yield of 4.89 g=54 percent. Concerning the product:

Melting point: 153°-154° C.

$^1$H-NMR: (CDCl$_3$, 300 MHz): 1.61, d, J=7 Hz, 3H; 3.45, dd, J=10.5 Hz, 1.4 Hz, 1H; 3.95, dd, J=10.5 Hz, 5 Hz, 1H; 4.21, d, J=9.5 Hz, 1H; 4.57, ddd, J=10.5 Hz, 9.5 Hz, 1.4 Hz, 1H 5.24, bs, 1H; 5.31, q, J=7 Hz, 1H; 7.4, m, 5H.

MS: (E.I. 70 ev) m/e 246 (30% M+), 231 (45%), 161 (28%), 105 (100%).

IR: (KBr) cm$^{-1}$ 3388, 1771 (s), 1669 (s), 1422, 1255, 699.

UV: (MeOH) λ max: 372 nm (ε=119); 256 nm (ε=764).

Elementary analysis for C$_{13}$H$_{14}$N$_2$O$_3$ (246.27): calculated: C 63.1%, H 5.7%, N 11.3%; found: C 63.4%, H 5.7%, N 11.4%.

[α]$_D^{20}$ [C=1 CHCl$_3$] +211.7°.

(2) Production of (3aS,6aR)-1-[(S)-(1-phenylethyl)]-dihydro-1H-furo-[3,4-d]-imidazol-2,4(3H,3aH)-dione A solution of 3.7 g (15.15 mmol) of 1-[(S)-(1-phenylethyl)]-1H-furo-[3,4-d]-imidazol-2,4(3H,6H)-dione in 100 ml of acetic acid is placed in a 250-ml autoclave and 0.4 g of palladium on activated carbon (5 percent) was added. Then the autoclave was flushed twice successively with hydrogen and filled to 50 bars. This mixture was stirred for 15 hours at room temperature. The catalyst was then filtered off. The solvent was evaporated at 20 mbars and the residue was chromatographed over silica gel with ethyl acetate. 2.0 g (54 percent yield) of the title product was eluted. Recrystallization in methanol yields white needles. Concerning the product: Melting point: 123°-125° C.

$^1$H-NMR: (CDCl$_3$, 300 MHz): δ 1.65, d, J=7.4 Hz, 3H; 4.08, d, J=8.6 Hz, 1H; 4.12, m, 1H; 4.37, dd, J=10.3 Hz, 4.8 Hz, 1H; 4.48, dd, J=10.2 Hz, 1.3 Hz, 1H; 5.36, q, J=7.3 Hz, 1H; 5.48, s, 1H.

MS: (E.I. 70 ev) m/e 246 (30% M+), 231 (45%), 161 (28%), 105 (100%).

[α]$_D^{20}$ [c=0, CHCl$_3$] −6.7%.

After that, the [3aR, 6aS] isomer was eluted in a yield of 1.05 g (28 percent).

EXAMPLE B (1) Production of (3aS, 6aR)-1-[(R)-(1-phenylethyl)]-3-benzyl-dihydro-1H-furo-[3,4-d]-imidazol-2,4(3H, 3aH)-dione 48 ml of dimethoxyethane and 0.39 g (16.2 mmol) of sodium hydride were placed in a 100-ml three-neck flask equipped with a magnetic stirrer under argon and with complete exclusion of moisture. Then 3.24 g (13.2 mmol) of (3aS, 6aR)-1-[(R)-(1-phenylethyl)]-dihydro-1H-furo[3,4-d]-imidazol-2,4(3H, 3aH)-dione was added. After a stirring time of 10 min., 2.76 g (16.2 mmol) of benzyl bromide was added and the suspension was stirred for 30 min. Then the reaction mixture was evaporated. The residue was dissolved with 25 ml of dichloromethane and 25 ml of water. The phases were separated and the aqueous phase was washed three times, each time with 15 ml of water. The organic phases were combined, dried with 5 g of magnesium sulfate and evaporated. (3aS, 6aR)-1-[R)-(1-phenylethyl)-3-benzyl-dihydro-1H-furo-[3,4-d]-imidazol-2,4(3H, 3aH)-dione was obtained as a beige product in a yield of 3.56 g (80.5 percent). Concerning the product: Melting point: 163°-164.5° C.

$^1$H-NMR: (CDCl$_3$, 300 MHz); δ 1.58, d, J=7 Hz, 3H; 3.38, dd, J=10 Hz, 3 Hz, 1H; 3.82, dd, J=10 Hz, 5 Hz, 1H; 3.89, d, J=9 Hz, 1H; 4.32, d, J=15 Hz, 1H; 4.44, ddd, J=9 Hz, 5 Hz, 3 Hz, 1H; 5.05, d, J=15 Hz, 1H; 5.36, q, J=7 Hz, 1H; 7.30-7.41, m 10 H.

MS: (E.I. 70 ev) m/e 336 (26%) M+, 321 (9%), 231 (22%), 187 (16%), 174 (14%), 105 (56%), 91 (100%).

Elementary analysis for C$_{20}$H$_{20}$N$_2$O$_3$ (336,39): calculated: C 71.4%; H 6.0%; N 8.3%. found: C71.3% H 6.2% N8.3%

[α]$_D^{20}$ [c=0.5 CHCl$_3$]+122.3°.

(2) Production of (3aS, 6aR)-1-[(R)-(1-phenylethyl)]-3-(4-methoxybenzyl)-dihydro-1H-furo-[3,4-d]-imidazol-2,4(3H, 3aH)-dione 9.75 g (0.22 mol) of sodium hydride (55 percent in oil) was added in 10 portions in 2 hours at −10° C. under argon to a solution of 50.0 g (0.2 mol) of (3aS, 6aR)-1-[(R)-(1-phenylethyl)]-dihydro-1H-furo-[3,4-d] -imidazol-2,4-(3H, 3aH)-dione and 39.8 g (0.25 mol) of 4-methoxybenzyl chloride in 500 ml of dried N,N-dimethylformamide. The reaction mixture was stirred at 5° C. for 2 hours and then at room temperature for another 2 hours. Then 8 ml of acetic acid was added. Then the mixture was evaporated to dryness. Then the residue was taken up in 100 ml of water and 200 ml of dichloromethane, the phases were separated and the aqueous phase was extracted twice with 100 ml of dichloromethane. The organic phases were dried over magnesium sulfate and concentrated. After suspension in ethanol with refluxing, cooling and filtering, 53.5 g (72 percent) of the title product was obtained in the form of white needles. Concerning the product: Melting point: 146.1°-146.4° C.

$^1$H-NMR: (CDCl$_3$, 300 Hz): δ 1.58, d, J=7 Hz, 3H; 3.37, dd, J=10 Hz, 3 Hz, 3H; 3.82, s, 3H; 3.82, dd, J=10

Hz, 5.5 Hz, 1H; 3.88, d, J=8.5 Hz, 1H; 4.25, d, J=14.5 Hz, 1H; 4.34, ddd, J=8.5 Hz, 5.5 Hz, 3H; 4.97, d, J=14.5 Hz, 1H; 5.34, q, J=7 Hz, 1H; 6.88, d, J=8.5 Hz, 2H; 7.32–7.38, m, 7H.

$[\alpha]_D^{20}$ [c=1 CHCl₃] +104.7°.

(3) Production of (3aS, 6aR)-1[(R)-(1-phenylethyl)]-3-tert-butoxycarbonyl-dihydro-1H-furo-[3,4-d]-imidazol-2,4(3H, 3aH)-dione 3.83 g (88 mmol) of sodium hydride (55 percent in oil) was added in 10 portions in 2 hours at −10° C. under argon to a solution of 20.0 g (81 mmol) of (3aS, 6 aR)-1(R)-(1-phenylethyl)]-dihydro-1H-furo-[3,4-d]-imidazol-2,4(3H, 3aH)-dione and 21.3 g (97 mmol) of di-tert-butyldicarbonate in 200 ml of dried N,N-dimethylformamide. The reaction mixture was stirred at 5° C. for 2 hours and then at room temperature for another 2 hours. Then 1 ml of acetic acid was added. Then the mixture was evaporated to dryness. The residue was taken up in 50 ml of water and 100 ml of dichloromethane, the phases were separated and the aqueous phase was extracted twice with 100 ml of dichloromethane. The organic phases were dried on magnesium sulfate and concentrated. After suspension in ethanol under fluxing, cooling and filtering, 25.8 g (92 percent) of the title product was obtained in the form of white needles. Concerning the product: Melting point: 177.4°–178.1° C.

¹H-NMR: (CDCl₃, 300 MHz): δ 1.59, s, 9H; 1.63, d, J=7.5 Hz, 3H; 3.51, d, J=11 Hz, 1H; 3.97, dd, J=11 Hz, 5 Hz, 1H; 4.50, dd, J=8 Hz, 5 Hz, 1H; 4.90, d, J=8 Hz, 1H; 5.39, q, J=7.5 Hz, 1H; 7.3–7.4 m 5H.

$[\alpha]_D^{20}$ ]c=1 CHCl₃] +55.8°.

(4) Production of (3aS, 6aR)-[(R)-(1-phenylethyl)]3-methoxymethyl-dihydro-1H-furo-[3,4-d]-imidazol-2,4-(3H, 3aH)-dione 4.0 g (93 mmol) sodium hydride (55 percent in oil) was added in 10 portions in 2 hours at −10° C. under argon to a solution of 19 g (77 mmol) of (3aS, 6aR)-[(R)-(1-phenylethyl)]-dihydro-1H-furo-[3,4-d]-imidazol-2,4-(3H, 3aH)-dione and 9.42 g (120 mmol) of chloromethyl methyl ether in 200 ml of dried N,N-dimethylformamide. The reaction mixture was stirred at 5° C. for 2 hours and then at room temperature for another 2 hours. Then 2 ml of acetic acid was added. Then the mixture was evaporated to dryness. Then the residue was taken up in 50 ml of water and 100 ml of dichloromethane, the phases were separated and the aqueous phase was extracted 2 times with 100 ml of dichloromethane. The organic phases were dried over magnesium sulfate and concentrated. After chromatographing the oily residue over silica gel with 500 ml of dichloromethane/ethyl acetate and concentrations of the fractions, 4.0 g (18 percent) of the title product was obtained as white powder. Concerning the product: Melting point: 96°–98° C.

¹H-NMR: (CDCl₃, 300 MHz): δ 1.61, d, J=7.5 Hz, 3H; 3.36, s, 3H; 3.41, dd, J=10 Hz, 3 Hz, 1H; 3.89, dd, J=10 Hz, 6 Hz, 1H; 4.36, d, J=9 Hz, 1H; 4.52, ddd, J=9 Hz, 6 Hz, 3 Hz, 1H; 4.87, d, J=11 Hz, 1H; 4.97, d, J=11 Hz, 1H; 5.34, q, J=7.5 Hz, 1H; 7.35–7.4, m, 5H.

EXAMPLE C

Production of (3aS, 6aR)-1-[(R)-(1-phenylethyl)]-3-benzyl-dihydro-1H-tieno-[3,4-d]-imidazol-2,4(3H, 3aH)-dione 2.03 g (6.03 mmol) of (3aS, 6aR)-1-[(R)-(1-phenylethyl)]-3-benzyl-dihydro-1H-furo-[3,4-d] -imidazol-2,4(3H, 3aH)-dione dissolved in 2 ml of dimethylacetamide was placed in a 25-ml flask, equipped with a magnetic stirrer and a ball condenser. The solution was heated to 150° C. and 0.81 g (7.14 mmol) of potassium thioacetate was added. After 45 min, the reaction mixture was allowed to cool and treated with 40 ml of toluene and 40 ml of water. The phases were separated; the toluene phase was washed three times with 20 ml of water and the combined aqueous phases were washed three times, each time with 30 ml of toluene. The toluene phases were combined, dried and evaporated. The resulting brown solid was washed with 5 ml of ether. Then the beige product, (3aR, 6aR)-1-[(R)-(1-phenylethyl)]-3-benzyl-dihydro-1H-thieno-[3,4-d]-imidazol-2,4(3H, 3aH)-dione was filtered off and dried. Concerning the product:

Yield: 1.82 g=85 percent.
Melting point: 144°–145° C.

¹H-NMR: (CDCl₃, 300 MHz): δ 1.67, d, J=7 Hz, 3H; 2.71, dd, J=12.5 Hz, 2.5 Hz, 1H; 3.03, dd, J=12.5 Hz, 5 Hz, 1H; 3.81, d, J=8 Hz, 1H; 4.34, d, J=15 Hz, 1H; 4.40, ddd, J=8 Hz, 5 Hz, 2.5 Hz, 1H; 5.04, d, J=15 Hz, 1H; 5.41, q, J=7 Hz, 1H; 7.30–7.50, m, 10H MS: (E.I. 70 ev) m/e 352 (1%) M⁺, 324 (30%), 278, (35%), 174 (80%), 146 (30%, 105 (70%), 91 (100%)

Elementary analysis for C₂₀H₂₀N₂O₂S (352.46): calculated C 68.2%, H5.7%, N7.9%, S 9.1%; found: C 67.9%, H 5.9%, N 8.0%.

$[\alpha]_D^{20}$ c=1.5 CHCl₃]°128.5°.

EXAMPLE D (1) Production of (3aS, 6aR)-hexahydro-1-[(R)-(1-phenylethyl)]-2-oxo-3-benzylthieno-[3,4-d]-imidazol-4-ylidene pentanoic acid 159.8 mg (3.66 mmol) of sodium hydride and 1.7 ml of dimethyl sulfoxide were placed in a 25-ml round-bottom flask. The suspension was heated with stirring and under argon to 70° C. It was stirred for 40 minutes more until, evolution of hydrogen was complete. The solution was cooled to room temperature and a solution of 801.5 mg (1.8 mmol) of (4-carboxybutyl)-triphenylphosphonium bromide in 1 ml of dimethyl sulfoxide was added. The dark red reaction mixture was stirred for 15 minutes and then added dropwise to a solution of 271 mg (0.77 mmol) of (3aS, 6 aR)-1-[(R)-(1-phenylethyl)]-3-benzyl-dihydro-1H-thieno-[3,4-d]-imidazol -2,4(3H, 6aH)-dione in 2 ml of dimethyl sulfoxide and 0.2 ml of toluene.

The reaction mixture was stirred for 2 hours at room temperature. Then 1 g of ice, 1 ml of conc, HCl and again 9 g of ice were added. After 5 minutes, 5 ml of water, 10 ml of benzene and 5 ml of ethyl acetate were added. Then the mixture was stirred for 1 hour at 60° C. The phases were separated. The brown organic phase was dried with 5 g of magnesium sulfate and separated with 4 preparative silica gel thin-layer plates (1 mm) by means of ethyl acetate. The product, (3aS, 6aR)-hexahydro-1-[(R)-(1-phenylethyl)-2-oxo-3-benzylthieno-[3,4-d]-imidazol-4-ylidene pentanoic acid, a colorless oil, was obtained in a yield of 38.2 mg (12 percent). Concerning the product:

$^1$H-NMR: (CDCl$_3$, 300 MHz); δ 1.58, d, J=7 Hz, 3H; 1.59, q, J=7 Hz, 2H; 1.98, m, 2H; 2.22, t, J=7.5 Hz, 2H; 2.29, dd, J=11.5 Hz, 4 Hz, 1H; 2.41, dd, J=11.5 Hz, 5 Hz, 1H; 3.97, d, J=15 Hz, 1H; 4.18, m, 2H; 4.84, d, J=15 Hz, 1H; 5.30, q, J=7 Hz, 1H; 5.31, t, J=7 Hz, 1H 7.10–7.40 m, 10H.

MS: (E.I. 70 ev) m/e 436 (55%) M+, 331 (55%), 252 (32%), 237 (60%), 120 (40%), 106 (100%).

(2) Production of (3aS, 6aR)-hexahydro-1-[(R)-(1-phenylethyl)-2-oxo-3-benzyl-thieno-[3,4-d]-imidazol-4-ylidene pentanoic acid 0.802 g (33 mmol) of magnesium chips were put into 5 ml of tetrahydrofuran. Then 2.37 g (11 mmol) of dibromobutane in 30 ml tetrahydrofuran was added in 1 hour. The reaction mixture was refluxed for 2 hours, then 2.55 g (22 mmol) of tetramethylethylenediamine was added and refluxed for another hour. To the suspension, cooled to 0° C., was then added 3.52 g (10 mmol) of (3aS, 6aR)-1-[(R)-(1-phenylethyl)]-3-benzyl-dihydro-1H-thieno-[3,4-d]-imidazol-2,4(3H, 3aH)-dione in 50 ml of tetrahydrofuran. Then the reaction mixture was stirred for 2 hours at room temperature and then cooled to 0° C. Carbon dioxide gas was introduced in 1 hour at 0° C. and 1 hour at room temperature. The reaction mixture was poured onto a mixture of 85 g of ice and 11.5 m of conc. hydochloric acid and then extracted with ethyl acetate. The combined organic phases were washed with water and saturated sodium chloride solution, dried with magnesium sulfate and finally concentrated. 50 mg of p-toluenesulfonic acid was added to the residue, which was then taken up in 170 ml of toluene. The reaction water was refluxed and distilled off by means of a water separator. The remaining toluene solution was concentrated and the resulting oil was chromotographed over silica gel with acetic acid ethyl ester/toluene. 1.22 g (28 percent) of the title product was obtained as a light yellowish oil.

(3) Production of (3aS,6aR)-hexahydro-1-[(R)-(1-phenylethyl)]-2-oxo-3-benzylthieno-[3,4-d]-imidazol-4-ylidene pentanoic acid 8.6 g of magnesium chips was placed in 75 ml of tetrahydrofuran. Then a mixture of 3.2 of 1,2-dibromoethane and 2.5 g of 1,4-dichlorobutane in 35 ml of tetrahydrofuran was added within 15 minutes so that the temperature could be kept between 30° and 35° C. Then another 20.5 g of 1,4-dichlorobutane in 75 ml of tetrahydrofuran was added within 30 minutes. The reaction mixture was stirred for 3 hours at this temperature and then mixed with 9 g of tetramethylethylenediamine and 180 ml of tetrahydrofuran. The reaction solution was cooled to −40° to −45° C. and then mixed with a solution of 30 g of (3aS,6aR)-1-[(R)-(1-phenylethyl)]-3-benzyl-dihydro-1H-thieno-[ 3,4-d]-imidazol-2,4(3H,3aH)-dione in 180 ml of tetrahydrofuran within 20 minutes. It was stirred at this temperature for 1 hour and then CO$_2$ gas was introduced for 30 minutes. The reaction mixture was poured onto 400 ml of 10 percent aqueous sulfuric acid and extracted several times with toluene. The toluene phase was mixed with 0.8 g of conc. Sulfuric acid, washed with water and concentrated on a rotary evaporator. The residue was mixed with 400 ml of 10 percent potassium carbonate solution and extracted with ethyl acetate. The organic phase was washed again with 10 percent potassium carbonate solution. The combined aqueous phases were adjusted to pH 7.3 with aqueous sulfuric acid and extracted several times with ethyl acetate. The organic phase was finally dried with magnesium sulfate and concentrated. The product was precipitated by addition of hexane, filtered off and dried. 32.5 g (89.3 percent) of the title product was obtained as snow-white powder with a content (HPLC) of more than 99 percent. Concerning the product: Melting point: 101.0°–102.0° C.

$[\alpha]_D^{20}$ [c=1.0 methanol]+253.8°.

EXAMPLE E (e) Production of (3aS,6aR)-hexahydro-1-[(R)-(1-phenylethyl)] -2-oxo-3-benzylthieno-[3,4-d]-imidazol-4-yl pentanoic acid A solution of 78.6 mg of (3aS,6aR)-hexahydro-1-[(R)-(1-phenylethyl)]-2-oxo-3-benzylthieno-[3,4-d]-imidazol-4-ylidene pentanoic acid in 5 ml of isopropanol was placed in a 100-ml autoclave and 39 mg of palladium (5 percent) on carbon added. The autoclave was flushed twice with hydrogen and the mixture was stirred under 50 bars of hydrogen pressure at 50° C. for 24 hours. Then the catalyst was filtered off and the solvent evaporated off. The product, (3aS,6aR)-hexahydro-1-[(R)-(1-phenylethyl)]-2-oxo-3-benzylthieno-[3,4-d]-imidazol-4-yl pentanoic acid, was obtained as a colorless oil in a yield of 56.1 mg (72 percent). Concerning the product:

$^1$H-NMR: (CDCl$_3$, 300 MHz): δ 1.57, m, 6H; 1.61, d, J=7 Hz, 3H; 2.13, m, 1H; 2.33, m, 2H; 3.03, m, 1H; 3.90, dd, J=10 Hz, 5 Hz, 1H; 3.94, d, J=15 Hz, 1H; 4.22, m, 1H; 5.06, d, J=15 Hz, 1H; 5.28, q, J=7 Hz, 1H; 7.20–7.40, m, 10H.

MS: (E.I. 70 ev) m/e 438 (13%), 423 (6%), 333 (16%), 187 (30%), 174 (15%), 105 (63%), 91 (100%).

EXAMPLE F

Production of d-biotin

A solution of 100 mg of (3aS,6aR)-hexahydro-1-[(R)-(1-phenylethyl)]-2-oxo-3-benzylthieno-[3,4-d]-imidazol-4-yl pentanoic acid in 4 ml of hydrobromic acid (48 percent) was heated in a 25-ml round-bottom flask for 3 hours at 120° C. with a vacuum of 400 mbars. After the reaction mixture was cooled, it was extracted with 5 ml of toluene. Then the aqueous phase was distilled off in a vacuum. The residue was dissolved in 10 ml of water and extracted with 10 ml of chloroform at 60° C. The aqueous phase was concentrated to 1 ml and cooled. d-(+) biotin precipitated in 40 mg of beige crystal (72 percent yield). Concerning the product: Melting point: 227°–229° C.

$[\alpha]_D^{25}$ [c=0.1 1N NaOH]+84.5°.

EXAMPLE 1

(a) Production of 3-phenylazotetronic acid [3-phenylazo-4-hydroxyfuran-2(5H)-one]

300 ml of 6N hydrochloric acid solution was placed in a 1.5-liter flask equipped with a 250-ml dropping funnel, a mechanical stirrer and a thermometer 57.6 g (0.61 mol) of distilled aniline was added with ice cooling. A solution of 43.92 g (0.64 mol) of sodium nitrite in 90 ml of ice water was added dropwise to the resulting suspension and stirred for 40 min. The resultant diazonium salt solution was added dropwise to a solution of 60 g (0.6 mol) of tetronic acid and 120 g (0.88 mol) of sodium acetate trihydrate in 900 ml of water for 30 min.

After this addition a yellow solid immediately precipitated. The reaction mixture was stirred at 10° C. for 1.5 hours, and filtered off; and the product was washed with 500 ml of cold methanol. It was dried at 35° C. in a vacuum. Concerning the product:

Yield: 113.2 g = 92.4 percent.
Melting point: 199°–200° C. (decomp.).

(b) Production of 3-phenylazo-4-[(S)-(1-phenylethylamino)]-furan-2(5H)-one 20.0 g (98 mmol) of 3-phenylazotetronic acid in 190 ml of toluene was suspended in a 500-ml three-neck flask equipped with a water separator, a thermometer and a magnetic stirrer, and was heated under argon to 80° C. Then 13.1 g (108 mmol) of (S)-phenylethylamine and 2.8 g (19 mmol) of triethyl borate were added. The solvent was refluxed under a vacuum of 300 mbar. After 7 hours, the toluene was evaporated. The black residue was washed with 100 ml of ether until a brown mass precipitated. The mass was triturated in ether and a yellowish product was obtained. The product, 3-phenylaxo-4[(S)-(1-phenylethylamino)]-furan-2(5H)-one, was filtered off and dried in a vacuum. Concerning the product:

Yield: 28.36 g = 94.0 percent.
Melting point: 114°–115° C.
NMR (CDCl$_3$, 300 MHz) δ in ppm: 1.69, d, J=7 Hz, 3H; 4.42, d, J=16 Hz, 1H; 4.45, bm, 1H; 4.81, d, J=16 Hz, 1H; 7.26–7.45, m, 8H; 7.78, d, J=8 Hz, 2H; 10.55, bs, 1H.
MS: (E.I. 70 ev) m/e 307 (9%) M+, 195 (25%), 171 (11%), 126 (10%), 105 (100%), 93 (28%).
IR: (KBr) cm$^{-1}$ 3064, 3026, 1746 (s), 1621 (s), 1456, 1356, 1288, 1045, 756.
UV: (MeOH) λ max: 366 nm (ε=21.050); 260 nm (ε=11.540); 235 nm (ε=12.800).
Elementary analysis for $C_{18}H_{17}N_3O_2$ (307.35): calculated: C 70.3%, H 5.6%; N 13.7%; found: C 70.3%, H 5.5%, N 13.4%.
$[\alpha]_D^{25}$ [c=1 CHCl$_3$] +785°.

(c) Production of 3-amino-4-[(S)-(1-phenylethylamino)]-furan-2(5H)-one 13.50 g (44 mmol) of 3-phenylazo-4-[(S)-(1-phenylethylamino)]-furan-2(5H)-one, 133 ml of acetic acid ethyl ester and 0.77 g of platinum on carbon (5 percent) were put into a 500-ml autoclave. The autoclave was closed and flushed twice with hydrogen while stirring. Then the reaction mixture was hydrogenated with hydrogen under 40 bars of pressure for 30 minutes. The catalyst was filtered off under argon and to the mother liquor was added dropwise with ice cooling, 130 ml of octane. 3-Amino-4-[(S)-(1-phenylethylamino)]-furan-2(5H)-one precipitated in the form of beige crystals. The product was dried under vacuum at room temperature. Concerning the product:

Yield: 8.53 g = 89.0 percent.
Melting point: 127.5°–128.0° C.
NMR: (CDCl$_3$, 300 MHz) δ in ppm: 1.55, d, J=7.0 Hz, 3H; 2.35, bs, 2H; 4.21, d, J=15 Hz, 1H; 4.51, d, q, J=7 Hz, 7 Hz, 1H; 4.53, d, J=15 Hz, 1H; 4.83, bd, J=7 Hz, 1H; 7.25–7.4, m, 5H.
MS: (E.I. 70 ev) m/e 218 (10%) M+, 114 (18%), 105 (100).
IR: (KBr) cm$^{-1}$ 3424, 3341 (s), 1737, 1651, 1584, 1428, 700.
UV: (MeOH) λ max 283 nm (ε=16.610).

Elementary analysis for $C_{12}H_{14}N_2O_2$ (218.26): calculated: C 66.0%, H 6.5%, N 12.8%; found: 66.2%, H 6.4%, N 12.8%.
$[\alpha]_D^{25}$ [c=1 CHCl$_3$] +20.5°.

(d) Production of 1-[(S)-1-phenylethyl)]-1H-furo-[3,4-d]-imidazol-2,4(3H, 6H)-dione 8.06 g (36 mmol) of 3-amino-4-[(S)-(1-phenylethylamino)]-furan-2(5H)-one and 65 ml tetrahydrofuran were placed in a 50-ml three-neck flask, which was equipped with a 50-ml dropping funnel and a magnetic stirrer, and were cooled to 0° C. Then a solution of 5.78 g (36 mmol) of chloroformic acid phenyl ester in 10 ml of tetrahydrofuran and a solution of 3.78 g (36 mmol) of triethylamine in 10 ml of tetrahydrofuran were added at the same time for 40 minutes. The white suspension was filtered and the light brown mother liquor was evaporated. The residue, a brown foam, was dissolved in 60 ml of acetonitrile and this solution was added in 40 minutes to a solution of 3.78 g (36 mmol) of triethylamine in 40 ml of acetonitrile, which was refluxed. The reaction mixture was evaporated and the residue washed with 50 ml of ether. The beige product, [1-(S)-(1-phenylethyl)]-1H-furo-[3,4-d]-imidazol-2,4(3H, 6H)-dione, was filtered off and dried in a vacuum. After recrystallization in methanol the product yield was 5.75 g = 66.0 percent. Concerning the product:

Melting point: 159°–160° C.
NMR: (CDCl$_3$, 300 MHz) in ppm: 1.77, d, J=7 Hz, 3H; 4.07, d, J=16 Hz, 1H; 4.72, d, J=16 Hz, 1H; 5.57, q, J=7 Hz, 1H; 7.35–7.58, m, 5H; 9.75, bs, 1H.
MS: (E.I. 70 ev) m/e 244 (16%), 105 (100%), 77 (37%).
IR: (KBr) cm$^{-1}$ 3250, 2981, 1761, 1700, 1482, 1450, 1340, 1268, 1000, 739, 705.
UV: (MeOH) λ max 266 nm (ε=12.900).
Elementary analysis for $C_{13}H_{12}O_2N_2$ (244.25): calculated: C 63.9%, H 4.9%, N 11.5%; found: C 63.6%, H 4.9%, N 11.3%.
$[\alpha]_D^{25}$ [c=1 CHCl$_3$] −69.5°.

EXAMPLE 2

(a) Production of 3-phenylazothiotetronic acid [3-phenylazo-4-hydroxythiophen-2(5H)-one or 2,3,4-trioxotetrahydrothiophene-3-phenylhydrazone]

28 ml of 6N hydrochloric acid solution was placed in a 100-ml beaker, which was equipped with a 100-ml dropping funnel, a thermometer and a mechanical stirrer. 5.02 g (53.9 mmol) of aniline was added with ice cooling. Then a solution of 3.81 g (55.2 mmol) of sodium nitrite in 21 ml of ice water was added dropwise to the resulting suspension in 30 min. with vigorous stirring. The resultant diazonium salt solution was added dropwise to a solution of 5.78 g (50 mmol) of thiotetronic acid in 49 ml of 1N sodium hydroxide solution at 5° C. with vigorous stirring in 30 minutes. At the same time 55 ml of 1N sodium carbonate solution was added to keep the pH of 7.0 constant. The mustard yellow product was filtered off, washed with 30 ml of water and dried in a vacuum. After recrystallization in toluene, the product yield was 10.5 g = 95.0 percent. Concerning the product:

Melting point: 195°–196.5° C.
NMR: (CDCl$_3$, 300 MHz) δ in ppm: 3.89, s, 2H; 3.95, s, 1H; 7.32, t, J=7 Hz, 2H; 7.46, t, J=7 Hz, 2H; 7.58, d, J=7 Hz, 2H; 3.89, s, 2H; 6.67, s, 1H; 7.32, t, J=7 Hz, 1H; 7.45, t, J=7 Hz, 2H; 7.57, d, J=7 Hz, 2H.

The tautomer ratio of 3-phenylazothiotetronic acid to 2,3,4-trioxotetrahydrothiophene-3-phenylhydrazone is 3 to 1.

MS: (E.I. 70 ev) m/e 220 (70%) M+, 143 (13%), 105 (31%) 92 (30%), 77 (100%).

IR: (KBr) cm$^{-1}$ 3450, 1688, 1673 s, 1532 s, 1465, 1424, 1397 s, 1129 s, 912 s, 764 s.

UV: (MeOH) λ max: 408 nm (ε=14.100); 372 (ε=16.700); 235 nm (ε=6.670).

Elementary analysis for $C_{10}H_8N_2O_2S$ (220.25): calculated: C 54.5%, H 3.7%, N 12.7%, S 14.6%; found: C 54.3%, H 3.5%, N 12.7%, S 14.8%.

(b) Production of 3-phenylazo-4-[(S)-(1)-phenylethylamino)]-thien-2(5H)-one 6.56 g (29.8 mmol) of 3-phenylazothiotetronic acid was dissolved in 165 ml of toluene with reflux under nitrogen in a 250-ml three-neck flask, which was equipped with a water separator, jacketed coil condensor and magnetic stirrer. Then 14.53 g (119.9 mmol) of (S-1-phenylethylamine was added and then in 40 minutes a solution of 2.19 g of boron trifluoride ethyl etherate in 5 ml of toluene was added. The reaction mixture was allowed to cool to room temperature. This reaction mixture was extracted with 100 ml of 0.9N hydrochloric acid, then with 50 ml of saturated sodium bicarbonate solution and then with 50 ml of saturated sodium sulfate solution. The dark brown solution was dried on 20 g of magnesium sulfate and evaporated. 50 ml of ether was added to the brown, viscous residue and allowed to rotate under slight vacuum. The resultant solid was dissolved in 6 ml of dichloromethane with reflux and recrystallized after the addition of 14 ml of ether at 0° C. After another recrystallization, the yield of 3-phenylazo-4-[(S)-(1-phenylethylamino)]-thien-2(5H)one was 5.99 g=58 percent. Concerning the product:

Melting point 129°-130° C.

NMR: (CDCl$_3$, 300 MHz) δ in ppm: 1.71, d, J=7 Hz, 3H; 3.64, d, J=17 Hz, 1H; 3.98, d, J=17 Hz, 1H; 4.77, d, q, J=7 Hz, 7 Hz, 1H; 7.25-7.5, m, 8H; 7.76, d, J=8 Hz, 2H; 12.34, bs, 1H.

MS (E.I. 70 ev) m/e 323 (10%) M+, 195 (22%), 105 (100%), 93 (30%), 77 (25%).

IR: (KBr) cm$^{-1}$ 3500 b, 1720, 1600 s, 1580 s, 1450, 1280.

UV: (MeOH) λ max: 410 nm (ε=9.600); 375 nm (ε=21.910); 290 nm (ε=11.880); 231 nm (ε=13.823).

Elementary analysis for $C_{18}H_{17}N_3OS$ (323.41): calculated: C 66.8%, H 5.3%, N13.0%, S 9.9%; found: C 66.7%, H 5.2%, N 13.2%, S 9.5%.

$[α]_D^{25}$ [c=1 CHCl$_3$] +889°.

(c) Production of 3-amino-4-[(S)-1(1-phenylethylamino)]-thien-2(5H)-one

A solution of 5.0 g (15.5 mmol) of 3-phenylazo-4-[(S)-(1-phenylethylamino)]-thien-2(5H)-one in 30 ml of tetrahydrofuran was placed in a 100-ml autoclave. Then 0.49 g of platinum on carbon 5 percent was added. The autoclave was flushed twice and the solution was hydrogenated with a hydrogen pressure of 30 bars for 45 minutes. The catalyst was filtered off under argon and to the mother liquor was added 90 ml of hexane with ice cooling. 3-Amino-4-[(S)-(1-phenylethylamino)]-thien-2(5H)-one precipitated as a beige, viscous oil. Concerning the product:

Yield: 2.4 g=65.0 percent.

NMR: (CDCl$_3$, 300 MHz), δ in ppm: 1.54, d, J=7 Hz, 3H; 3.30, bs, 3-4H; 3.37, d, J=16.5 Hz, 1H; 3.72, d, J=16.5 Hz, 1H; 4.60, q, J=7 Hz, 1H; 7.22-7.37, m, 5H.

MS (E.I. 70 ev) m/e 234 (4%), M+, 130 (18%), 105 (100%).

(d) Production of (S)-(1-phenylethyl)-1H-thieno-[3,4-d]-imidazol-2,4(3H,6H)-dione 22 ml of tetrahydrofuran was placed in a 250-ml three-neck flask equipped with two 50-ml dropping funnels, a thermometer and a magnetic stirrer. It was cooled to 0° C. and 11.1 ml of 1.25M phosgene solution in toluene (13.87 mmol) was added under argon. At the same time a solution of 3.24 g (13.82 mmol) of 3-amino-4-[(S)-(1-phenylethylamino)]-thien-2(5H)-one in 10 ml of tetrahydrofuran was added and a solution of 2.18 g (27.75 mmol) of triethylamine in 10 ml of tetrahydrofuran was added in 3 hours at 5° C. To it was added 10 ml of 5 percent aqueous ammonia solution. The tetrahydrofuran was evaporated and the aqueous residue was extracted three times with 10 ml of dichloromethane. The solution was evaporated and chromatographed by 100 g of silica gel with 700 ml of ethyl acetate. The yield of (S)-(1-phenylethyl)-thieno-[3,4-d]-imidazol-2,4(3H, 6H)-dione (beige crystals) was 2.16 g=60 percent.

Melting point: 218°-220° C.

MNR: (CDCl$_3$, 300 MHz) δ in ppm: 1.83, d, J=7 Hz, 3H; 3.23, d, J=16.5 Hz, 1H; 3.86, d, J=16.5 Hz, 1H; 5.73, q, J=7 Hz, 1H; 7.40, m, 5H; 8.78, bs, 1H.

MS: (E.I. 70 ev) m/e 260 (4%) M+, 156 (4%), 105 (100%), 79 (105), 77 (12%).

IR: (KBr) cm$^{-1}$ 3225, 2945, 2918, 1702 s, 1619, 1451, 1351, 1268.

UV: (MeOH) λ max: 297 nm (ε=9.805); 248 nm (ε=5.960).

Elementary analysis for $C_{13}H_{12}N_2O_2S$ (260.31): calculated: C 60.0%, H 4.7%, N 10.7%, S 12.3%; found: C 59.5%, H 4.7%, N 10.8%, S 12.0%.

$[α]_D^{25}$ [c=1 CHCl$_3$] −63.2°.

(e) Production of 1-[(S)-(1-phenylethyl)]-3-acetyl-1H-thieno-[3,4-d]-imidazol-2,4(3H, 6H)-dione 0.5 g (1.94 mmol) of 1-[(S)-(1-phenylethyl)]-1H-thieno-[3,4-d]-imidazol-2,4(3H, 6H)-dione in 20 ml of acetic acid anhydride was heated in a 25-ml flask at 50° C. for 3 hours. Then the solvent was evaporated and the residue washed with 3 ml of ether. The beige product was then dried. The yield of 1-[(S)-(1-phenylethyl)-3-acetyl-1H-thieno-[3,4-d]-imidazol-2,4(3H,6H)-dione was 0.43 g=73.0 percent. Concerning the product:

Melting point 187°-189.5° C.

NMR: (CDCl$_3$, 300 MHz) δ in ppm: 1.85, d, J=7 Hz, 3H; 2.71, s, 3H; 3.18, d, J=17.5 Hz, 1H; 3.83, d, J=17.5 Hz, 1H; 5.71, q, J=7 Hz, 1H; 7.35-7.45, m, 5H.

MS: (E.I. 70 ev) m/e 302 (1%) M+, 260 (10%), (−CH$_2$CO), 165 (5%), 105 (100%), 43 (20%).

IR: (KBr) cm$^{-1}$ 2920, 1736 s, 1447, 1376, 1354, 1298.

UV: (MeOH) λ max; 297 nm (ε=11.480) 248 nm (ε=6.930)

Elementary analysis for $C_{15}H_{14}O_3N_2S$ (302.35): calculated: C59.6%, H 4.7%, N 9.3%, S 10.6%; found: C 58.9%, H 4.7%, N 9.2%, S 10.3%. $[α]_D^{25}$ [c=1 CHCl$_3$]−63.3°.

EXAMPLE 3

Production of 1-[(S)-(1-phenylethyl)]-3-benzyl-1H-thieno-[3,4-d]-imidazol-2,4(3H,6H)-dione To a suspension of 75 mg (3.1 mmol) of sodium hydride in 15 ml of tetrahydrofuran were added 0.73 g (2.8 mmol) of 1-[(S)-(1-phenylethyl)]-1H-thieno-[3,4-d]-imidazole-2,4(3H,6H)-dione, 0.54 g (3.2 mmol) of benzyl bromide and 10 ml of diethylene glycol diethyl ether. The reaction mixture was refluxed for 12 hours. The solvent was evaporated in a vacuum and the residue separated between 10 ml of dichloromethane and 10 ml of water. The aqueous phase was washed twice with 10 ml of dichloromethane. The organic phases were combined, dried with 10 g of magnesium sulfate and evaporated. The solid residue was washed with 5 ml of ether, filtered off and dried. The yield of 1-[(S)-(1-phenylethyl)]-3-benzyl-1H-thieno-[3,4-d]-imidazol 2,4(3H,6H)-dione was 57.0 mg=60 percent. Concerning the product:

Melting point: 143°–145° C.

NMR: (CDCl$_3$, 300 MHz) δ in ppm: 1.79, d, J=7 Hz, 3H; 3.18, d, J=17 Hz, 1H; 3.78, d, J=17 Hz, 1H; 5.03, s, 2H, 5.21, J=7 Hz, 1H 7.27–7.4, m, 8H, 7.49, d, J−8 Hz, J=1.5 Hz, 2H;

MS: (E.I. 70 ev) m/e 350 (4%) M$^+$, 246 (12%), 105, (100%), 91 (40%),

IR: (KBr) cm$^{-1}$ 2982, 1707 s, 1672 s, 1456, 1346, 846, 700.

UV: (MeOH) λ max: 285.8 nm (ε=10.200).

What is claimed is:

1. (3aS, 6aR)-[(R)-(1-phenylethyl)]-3-4-methoxybenzyl dihydro-1H-furo-[3,4-d]-imidazol-2,4(3H,3aH)-dione

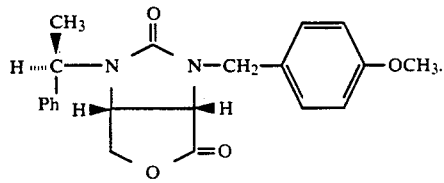

2. 1H-furo-[3,4-d]-imidazol-2,5-(3H,3aH)-dione of the formula

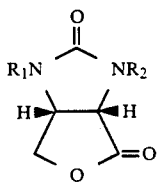

II wherein R$_1$ is an (R)$^-$ or (S)-1-phenylethyl group and R$_2$ is hydrogen.

* * * * *